(12) United States Patent
Pozniak et al.

(10) Patent No.: US 6,508,797 B1
(45) Date of Patent: Jan. 21, 2003

(54) PANT-LIKE DISPOSABLE ABSORBENT ARTICLES WITH A RELEASABLE LINE OF WEAKNESS AND A FASTENER

(75) Inventors: Jennifer Elizabeth Pozniak, Appleton; Timothy James Blenke, Neenah, both of WI (US); Cassandra Elizabeth Morris, Charlottesville, VA (US); Thomas Harold Roessler, Menasha, WI (US); Jody Dorothy Suprise, Pine River, WI (US); Robert Eugene Vogt, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 26 days.

(21) Appl. No.: 09/706,150

(22) Filed: Nov. 3, 2000

(51) Int. Cl.$^7$ ................................................. A61F 13/15
(52) U.S. Cl. ................... 604/385.11; 604/386; 604/389; 604/391
(58) Field of Search ........................... 604/385.11, 386, 604/389, 391

(56) References Cited

U.S. PATENT DOCUMENTS 1,079,479 A 11/1913 Earnshaw (List continued on next page.)

FOREIGN PATENT DOCUMENTS

| AU | 667899 | 4/1996 |
|---|---|---|
| CA | 2096672 | 11/1993 |
| CA | 2103992 A1 | 2/1994 |
| CA | 2187021 A1 | 10/1995 |

(List continued on next page.)

OTHER PUBLICATIONS

Derwent World Patent Database abstract of FR 2762507 A1: Description of RAHALA, "Baby's Disposable Nappy."

(List continued on next page.)

*Primary Examiner*—Andy Falik
(74) *Attorney, Agent, or Firm*—Jeffrey B. Curtin; Alyssa A. Dudkowski

(57) ABSTRACT

A pant-like, disposable absorbent article includes an absorbent chassis, a pair of opposed side panels, at least one line of weakness and at least one fastener. The absorbent chassis defines a pair of laterally opposed side edges and a pair of longitudinally opposed waist edges. The side panels extend between the side edges of the absorbent chassis to define a waist opening and a pair of leg openings in the pant-like disposable absorbent article. Each of the opposed side panels defines a first side margin which is permanently attached to the side edge of the absorbent chassis in one waist region of the absorbent article to provide a front permanent joint. The opposed side panels further define a second side margin opposite the first side margin which is permanently attached to the side edge of the absorbent chassis in the other waist region of the absorbent article to provide a back permanent joint. The fastener and the line of weakness are located in one of the side panels, with the line of weakness separating the fastener from one of the permanent joints. The fastener is configured to be released and used to refastenably engage the at least one side panel to the opposite waist region of the absorbent article after the line of weakness is broken.

33 Claims, 6 Drawing Sheets

U.S. PATENT DOCUMENTS

| | | |
|---|---|---|
| 1,485,001 A | 2/1924 | Wills |
| 1,657,909 A | 1/1928 | Abramovich |
| 1,705,194 A | 3/1929 | Marinsky |
| 1,762,468 A | 6/1930 | Brewer |
| 1,963,334 A | 6/1934 | Neilson |
| 2,201,255 A | 5/1940 | Wilson, Jr. |
| 2,242,977 A | 5/1941 | Marcos |
| 2,475,175 A | 7/1949 | Cadous |
| 2,477,914 A | 8/1949 | Webb |
| 2,545,761 A | 3/1951 | Brink |
| 2,570,963 A | 10/1951 | Mesmer |
| 2,630,120 A | 3/1953 | Neilson |
| 2,630,806 A | 3/1953 | Kiscaden |
| 2,743,725 A | 5/1956 | Matthews |
| 2,801,632 A | 8/1957 | Burner et al. |
| 2,808,831 A | 10/1957 | Winslett |
| 2,830,589 A | 4/1958 | Doner |
| 2,833,282 A | 5/1958 | Moore |
| 2,910,982 A | 11/1959 | Woodward |
| 2,931,361 A | 4/1960 | Sostrin |
| 3,039,466 A | 6/1962 | Wilson |
| 3,077,193 A | 2/1963 | Mann |
| 3,610,244 A | 10/1971 | Jones, Sr. |
| 3,638,651 A | 2/1972 | Torr |
| 3,653,381 A | 4/1972 | Warnken |
| 3,825,006 A | 7/1974 | Ralph |
| 3,882,871 A | 5/1975 | Taniguchi |
| 4,024,867 A | 5/1977 | Mesek |
| 4,051,853 A | 10/1977 | Egan, Jr. |
| 4,051,854 A | 10/1977 | Aaron |
| 4,066,081 A | 1/1978 | Schaar |
| 4,074,716 A | 2/1978 | Schaar |
| 4,089,068 A | 5/1978 | Swallow |
| 4,090,516 A | 5/1978 | Schaar |
| 4,205,679 A | 6/1980 | Repke et al. |
| 4,210,143 A | 7/1980 | De Jonckheere |
| 4,315,508 A | 2/1982 | Bolick |
| 4,337,771 A | 7/1982 | Pieniak et al. |
| 4,409,049 A | 10/1983 | Passafiume et al. |
| 4,410,327 A | 10/1983 | Baggaley |
| 4,500,316 A | 2/1985 | Damico |
| 4,515,595 A | 5/1985 | Kievit et al. |
| 4,522,853 A | 6/1985 | Szonn et al. |
| 4,525,407 A | 6/1985 | Ness |
| 4,563,185 A | 1/1986 | Reiter |
| 4,568,341 A | 2/1986 | Mitchell et al. |
| 4,581,772 A | 4/1986 | Smith |
| 4,596,055 A | 6/1986 | Aach et al. |
| 4,598,528 A | 7/1986 | McFarland et al. |
| 4,604,096 A | 8/1986 | Dean et al. |
| 4,610,680 A | 9/1986 | LaFleur |
| 4,610,681 A | 9/1986 | Strohbeen et al. |
| 4,615,695 A | 10/1986 | Cooper |
| 4,617,022 A | 10/1986 | Pigneul et al. |
| 4,619,649 A | 10/1986 | Roberts |
| 4,623,339 A | 11/1986 | Ciraldo et al. |
| 4,630,320 A | 12/1986 | Van Gompel |
| 4,663,220 A | 5/1987 | Wisneski et al. |
| 4,675,918 A | 6/1987 | O'Brien |
| D290,780 S | 7/1987 | Wistrand |
| 4,699,622 A | 10/1987 | Toussant et al. |
| 4,704,116 A | 11/1987 | Enloe |
| 4,726,874 A | 2/1988 | Van Vliet |
| 4,728,326 A | 3/1988 | Gilles |
| 4,743,239 A * | 5/1988 | Cole .................... 604/385.23 |
| 4,747,846 A | 5/1988 | Boland et al. |
| 4,753,646 A | 6/1988 | Enloe |
| 4,753,650 A | 6/1988 | Williams |
| 4,798,603 A | 1/1989 | Meyer et al. |
| 4,801,485 A | 1/1989 | Sallee et al. |
| 4,808,252 A | 2/1989 | Lash |
| 4,826,499 A | 5/1989 | Ahr |
| 4,850,988 A | 7/1989 | Aledo et al. |
| 4,850,992 A | 7/1989 | Amaral et al. |
| 4,857,067 A | 8/1989 | Wood et al. |
| 4,883,481 A | 11/1989 | Blanchard |
| 4,892,598 A | 1/1990 | Stevens et al. |
| 4,895,569 A | 1/1990 | Wilson et al. |
| 4,904,252 A | 2/1990 | Fitzgerald |
| 4,908,247 A | 3/1990 | Baird et al. |
| 4,909,802 A | 3/1990 | Ahr et al. |
| 4,911,702 A | 3/1990 | O'Leary et al. |
| 4,917,682 A | 4/1990 | Lancaster et al. |
| 4,936,840 A | 6/1990 | Proxmire |
| 4,937,887 A | 7/1990 | Schreiner |
| 4,938,753 A | 7/1990 | Van Gompel et al. |
| 4,944,733 A | 7/1990 | Casale |
| 4,961,736 A | 10/1990 | McCloud |
| 4,964,860 A | 10/1990 | Gipson et al. |
| 4,973,326 A | 11/1990 | Wood et al. |
| 4,988,346 A | 1/1991 | Pfefferkorn |
| 4,998,929 A | 3/1991 | Bjorksund et al. |
| 5,019,072 A | 5/1991 | Polski |
| 5,019,073 A | 5/1991 | Roessler et al. |
| 5,040,244 A | 8/1991 | Tubbs |
| 5,062,839 A | 11/1991 | Anderson |
| 5,066,289 A | 11/1991 | Polski |
| 5,069,678 A | 12/1991 | Yamamoto et al. |
| 5,074,854 A * | 12/1991 | Davis .................... 604/385.11 |
| 5,087,253 A | 2/1992 | Cooper |
| 5,106,382 A | 4/1992 | Henry |
| 5,106,385 A | 4/1992 | Allen et al. |
| 5,110,403 A | 5/1992 | Ehlert |
| 5,112,326 A | 5/1992 | Quadrini |
| 5,135,522 A | 8/1992 | Fahrenkrug et al. |
| 5,140,757 A | 8/1992 | Terada |
| 5,163,932 A | 11/1992 | Nomura et al. |
| 5,170,505 A | 12/1992 | Rohrer |
| 5,176,668 A | 1/1993 | Bernardin |
| 5,176,670 A | 1/1993 | Roessler et al. |
| 5,176,672 A | 1/1993 | Bruemmer et al. |
| 5,185,011 A | 2/1993 | Strasser |
| 5,186,779 A | 2/1993 | Tubbs |
| 5,187,817 A | 2/1993 | Zolner |
| 5,192,606 A | 3/1993 | Proxmire et al. |
| 5,226,992 A | 7/1993 | Morman |
| 5,236,430 A | 8/1993 | Bridges |
| 5,242,436 A | 9/1993 | Weil et al. |
| 5,246,433 A | 9/1993 | Hasse et al. |
| 5,275,590 A | 1/1994 | Huffman et al. |
| 5,300,057 A | 4/1994 | Miller et al. |
| 5,304,162 A | 4/1994 | Kuen |
| 5,312,387 A | 5/1994 | Rossini et al. |
| 5,340,431 A | 8/1994 | Terada |
| 5,358,500 A | 10/1994 | Lavon et al. |
| 5,368,584 A | 11/1994 | Clear et al. |
| 5,368,585 A | 11/1994 | Dokken |
| 5,370,632 A | 12/1994 | Beplate |
| 5,370,634 A | 12/1994 | Ando et al. |
| 5,373,587 A | 12/1994 | Sexton |
| 5,374,262 A | 12/1994 | Keuhn, Jr. et al. |
| 5,383,872 A | 1/1995 | Roessler et al. |
| 5,386,595 A | 2/1995 | Kuen et al. |
| 5,397,639 A | 3/1995 | Tollini |
| 5,399,219 A | 3/1995 | Roessler et al. |
| 5,401,275 A | 3/1995 | Flug et al. |
| 5,409,476 A | 4/1995 | Coates |
| 5,423,789 A | 6/1995 | Kuen |
| 5,445,628 A | 8/1995 | Gipson et al. |
| 5,451,219 A | 9/1995 | Suzuki et al. |
| 5,462,541 A | 10/1995 | Bruemmer et al. |

| | | | | | | |
|---|---|---|---|---|---|---|
| 5,489,282 A | 2/1996 | Zehner et al. | | 5,919,334 A | 7/1999 | Niedermeyer |
| 5,496,298 A | 3/1996 | Kuepper et al. | | 5,944,707 A | 8/1999 | Ronn |
| 5,499,978 A | 3/1996 | Buell et al. | | 5,961,761 A | 10/1999 | Heindel et al. |
| 5,500,063 A | 3/1996 | Jessup | | 5,971,153 A | 10/1999 | Bauer et al. |
| 5,509,915 A | 4/1996 | Hanson et al. | | 6,022,430 A | 2/2000 | Blenke et al. |
| 5,527,302 A | 6/1996 | Endres et al. | | 6,022,431 A | 2/2000 | Blenke et al. |
| H1558 H | 7/1996 | Goulait et al. | | 6,022,432 A | 2/2000 | Elsberg et al. |
| 5,531,731 A | 7/1996 | Brusky | | 6,030,373 A | 2/2000 | VanGompel et al. |
| 5,531,732 A | 7/1996 | Wood | | 6,036,805 A | 3/2000 | McNichols |
| 5,537,722 A | 7/1996 | Niederhofer et al. | | 6,045,543 A | 4/2000 | Pozniak et al. |
| 5,540,796 A | 7/1996 | Fries | | 6,113,717 A | 9/2000 | Vogt et al. |
| 5,545,158 A | 8/1996 | Jessup | | 6,149,638 A | 11/2000 | Vogt et al. |
| 5,545,275 A | 8/1996 | Herrin et al. | | 6,287,287 B1 | 9/2001 | Elsberg |
| 5,549,592 A | 8/1996 | Fries et al. | | 6,322,552 B1 * | 11/2001 | Blenke et al. .............. 604/391 |
| 5,554,146 A | 9/1996 | Niederhofer et al. | | | | |

FOREIGN PATENT DOCUMENTS

| | | | |
|---|---|---|---|
| 5,562,650 A | 10/1996 | Everett et al. | |
| 5,569,232 A | 10/1996 | Roe et al. | CA 2187366 A1 10/1995 |
| 5,569,234 A | 10/1996 | Buell et al. | EP 0 206 208 B1 12/1986 |
| 5,571,586 A | 11/1996 | Gobran | EP 0 217 032 B1 4/1987 |
| 5,575,784 A | 11/1996 | Ames-Ooten et al. | EP 0 251 251 A2 1/1988 |
| 5,582,606 A | 12/1996 | Bruemmer et al. | EP 0 463 276 A1 1/1992 |
| 5,591,152 A | 1/1997 | Buell et al. | EP 0 532 034 B1 3/1993 |
| 5,593,401 A | 1/1997 | Sosalla et al. | EP 0 544 703 B1 6/1993 |
| 5,601,546 A | 2/1997 | Tanji et al. | EP 0 696 911 B1 2/1996 |
| 5,605,735 A | 2/1997 | Zehner et al. | EP 0 753 292 A2 1/1997 |
| 5,607,416 A | 3/1997 | Yamamoto et al. | EP 0 487 758 B1 3/1997 |
| 5,611,789 A | 3/1997 | Seth | EP 0 597 331 B1 11/1997 |
| 5,618,366 A | 4/1997 | Suekane | EP 0 809 992 A1 12/1997 |
| 5,624,420 A * | 4/1997 | Bridges et al. .............. 156/290 | EP 0 878 180 A2 11/1998 |
| 5,624,424 A | 4/1997 | Saisaka et al. | FR 2566631 1/1986 |
| 5,624,428 A | 4/1997 | Sauer | GB 1 520 740 8/1978 |
| 5,624,429 A | 4/1997 | Long et al. | GB 2 244 422 B 12/1991 |
| 5,626,574 A | 5/1997 | Sasaki et al. | GB 2 267 024 B 11/1993 |
| 5,628,738 A | 5/1997 | Suekane | GB 2 288 314 A 10/1995 |
| 5,629,063 A | 5/1997 | Gobran | GB 2 288 315 A 10/1995 |
| 5,634,916 A | 6/1997 | Lavon et al. | GB 2 288 316 A 10/1995 |
| H1674 H | 8/1997 | Ames et al. | GB 2 291 783 A 2/1996 |
| 5,656,111 A | 8/1997 | Dilnik et al. | GB 2 294 867 A 5/1996 |
| 5,662,637 A | 9/1997 | Kitaoka et al. | GB 2 297 473 A 6/1996 |
| 5,662,638 A | 9/1997 | Johnson et al. | GB 2 308 290 A 6/1997 |
| 5,665,084 A | 9/1997 | Richmond | JP 6-77718 U 11/1994 |
| 5,669,897 A | 9/1997 | Lavon et al. | JP 7-213553 A 8/1995 |
| 5,685,873 A | 11/1997 | Bruemmer | JP 7-227407 A 8/1995 |
| 5,685,874 A | 11/1997 | Buell et al. | JP 7-255773 A 10/1995 |
| 5,690,626 A | 11/1997 | Suzuki et al. | JP 7-299094 A 11/1995 |
| 5,690,627 A | 11/1997 | Clear et al. | JP 8-229072 A 9/1996 |
| 5,693,038 A | 12/1997 | Suzuki et al. | JP 9-287 U 5/1997 |
| 5,695,488 A | 12/1997 | Sosalla | JP 11-47188 A 2/1999 |
| 5,695,868 A | 12/1997 | McCormack | WO WO 83/04163 A1 12/1983 |
| D389,320 S | 1/1998 | Vinnage et al. | WO WO 90/07313 A1 7/1990 |
| 5,707,364 A | 1/1998 | Coates | WO WO 91/04724 A1 4/1991 |
| 5,711,832 A | 1/1998 | Glaug et al. | WO WO 91/08725 A1 6/1991 |
| 5,725,518 A | 3/1998 | Coates | WO WO 92/22274 A1 12/1992 |
| 5,759,317 A | 6/1998 | Justmann | WO WO 93/09742 A1 5/1993 |
| 5,772,649 A | 6/1998 | Siudzinski | WO WO 94/17768 A1 8/1994 |
| 5,772,825 A | 6/1998 | Schmitz | WO WO 95/01148 A1 1/1995 |
| 5,788,685 A | 8/1998 | Ronnberg et al. | WO WO 95/02383 A1 1/1995 |
| 5,788,797 A | 8/1998 | Herrin et al. | WO WO 95/13772 A1 5/1995 |
| 5,795,433 A | 8/1998 | Niedermeyer | WO WO 95/22951 A1 8/1995 |
| 5,827,259 A | 10/1998 | Laux et al. | WO WO 95/27460 A1 10/1995 |
| 5,827,260 A | 10/1998 | Suzuki et al. | WO WO 95/27462 A1 10/1995 |
| 5,830,206 A | 11/1998 | Larsson | WO WO 95/29657 A1 11/1995 |
| 5,843,056 A | 12/1998 | Good et al. | WO WO 96/03101 A1 2/1996 |
| 5,855,574 A | 1/1999 | Kling et al. | WO WO 96/18315 A1 6/1996 |
| 5,876,531 A | 3/1999 | Jacobs et al. | WO WO 96/29037 A1 9/1996 |
| 5,897,545 A | 4/1999 | Kline et al. | WO WO 96/32084 A1 10/1996 |
| 5,899,896 A | 5/1999 | Suprise et al. | WO WO 97/15260 A1 5/1997 |
| 5,904,673 A | 5/1999 | Roe et al. | WO WO 97/23186 A1 7/1997 |
| 5,904,802 A | 5/1999 | Niedermeyer | WO WO 97/25951 A1 7/1997 |
| 5,916,203 A | 6/1999 | Brandon et al. | WO WO 97/31605 A1 9/1997 |
| 5,916,207 A | 6/1999 | Toyoda et al. | WO WO 97/32555 A1 9/1997 |

| | | |
|---|---|---|
| WO | WO 97/33547 A1 | 9/1997 |
| WO | WO 97/46197 A1 | 12/1997 |
| WO | WO 97/47265 A1 | 12/1997 |
| WO | WO 97/48357 A1 | 12/1997 |
| WO | WO 98/03140 A1 | 1/1998 |
| WO | WO 98/18421 A1 | 5/1998 |
| WO | WO 98/29251 A1 | 7/1998 |
| WO | WO 98/51252 A1 | 11/1998 |
| WO | WO 98/56328 A1 | 12/1998 |
| WO | WO 99/07319 A1 | 2/1999 |
| WO | WO 99/56688 A1 | 11/1999 |
| WO | WO 99/65438 A1 | 12/1999 |
| WO | WO 99/65442 A1 | 12/1999 |
| WO | WO 00/35395 A2 | 6/2000 |
| WO | WO 00/37009 A2 | 6/2000 |
| WO | WO 00/37010 A1 | 6/2000 |
| WO | WO 01/43682 A1 | 6/2001 |
| WO | WO 01/43683 A1 | 6/2001 |
| WO | WO 01/70155 A1 | 9/2001 |

OTHER PUBLICATIONS

Derwent World Patent Database abstract of JP 6–063076 A: Description of Kao Corp. (Kaos), "Throw Away Diaper Or Nappy."

Derwent World Patent Database abstract of JP 95–044941 B2: Description of ZUIKO KK (ZUIK–N), "Simple Solid Diaper For Eliminating Waste of Material by Using Square Shape."

Derwent World Patent Database abstract of JP 9–276334 A: Description of Kao Corp (Kaos), "Disposable Baby Nappy."

Derwent World Patent Database abstract of JP 11–070143 A: Description of TOYO EISAI KK (TOEI–N), "Disposable Diaper For Adults And Children."

Derwent World Patent Database abstract of JP 11–076299 A: Description of UNI–CHARM KK (UNIC–N), "Disposable Diaper."

* cited by examiner

PANT-LIKE DISPOSABLE ABSORBENT ARTICLES WITH A RELEASABLE LINE OF WEAKNESS AND A FASTENER

FIELD OF THE INVENTION

The present invention relates to disposable absorbent articles which are adapted to contain body exudates. More particularly, the present invention relates to pant-like disposable absorbent articles having at least one line of weakness and a fastener.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and clean manner without undesirably soiling the caregiver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. In such circumstances it is further desirable that the caregiver or the wearer may be able to apply the absorbent article to a wearer in a prone position similar to a conventional diaper. Such absorbent articles can assist in the toilet training of children.

Conventional diapers are not provided in a prefastened condition and have typically included a front waist portion and a back waist portion which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost corners of the diaper in the back waist region of the diaper and a complimentary fastener, such as a taping panel, located on the exterior surface of the outer cover of the diaper in the front waist portion of the diaper. In such a configuration, the diaper has been positioned between the legs of the wearer while the wearer is lying down and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the caregiver. However, such conventional diapers are not provided in a pant-like, prefastened configuration and, thus, are not configured to be pulled up or down over the hips of the wearer when the fasteners are attached.

Several attempts have been made to provide absorbent articles which effectively contain body exudates and are capable of being pulled up or down over the hips of the wearer. For example, some conventional absorbent articles, such as conventional training pants, have included integral side panels which connect the front waist portion to the back waist portion of the absorbent article. The side panels have been made stretchable such that the waist opening of the absorbent article can expand to allow the absorbent article to be pulled up or down over the hips of the wearer if desired. Such side panels have also been designed such that they may be torn to remove the training pant from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely which can undesirably result in leaks. As a result, many of such articles have not contained bodily exudates as effectively as conventional diaper-type articles which can be adjusted to achieve a more conforming fit to the wearer. Moreover, the inspection and removal of soiled absorbent articles which have integral side panels, such as conventional training pants, have not always been completely satisfactory. For example, the side panels have been difficult to tear when attempting to remove the article from the waist of the wearer instead of pulling the article down over the hips of the wearer. Finally, most of these conventional training pants do not provide the option of being applied as a conventional diaper.

Accordingly, despite the attempts to develop improved absorbent articles, there remains a need for absorbent articles which can effectively provide the benefits of both conventional training pants and conventional diapers. That is, there remains a need for absorbent articles which conform to the wearer to effectively contain bodily exudates, which are capable of being pulled up and down over the hips and buttocks of the wearer without opening, which are readily secured about and removed from the wearer in a convenient and clean manner and which allow easy inspection by the care giver to assist in determining whether the article is soiled. Moreover, there is a need that such pant-like disposable absorbent articles are also capable of being applied in the manner of a conventional diaper, to a wearer lying in a prone position.

SUMMARY OF THE INVENTION

In response to the difficulties and problems discussed above, new pant-like disposable absorbent articles which have at least one line of weakness and at least one fastener have been discovered. In one aspect, the present invention concerns a pant-like, disposable absorbent article which defines a front waist region, a back waist region, a crotch region which extends between and connects the waist regions, a longitudinal direction and a lateral direction. The absorbent article includes an absorbent chassis which defines an absorbent core, an exterior surface, an interior surface opposite the exterior surface, a pair of laterally opposed side edges and a pair of longitudinally opposed waist edges. The absorbent article also includes a pair of opposed side panels which extend laterally outward from the side edges of the absorbent chassis and connect the front waist region and back waist region to define a waist opening. and a pair of leg openings in the pant-like disposable absorbent article. Each of the side panels define a first side margin which is permanently attached to the side edge of the absorbent chassis in the front waist region of the absorbent article to provide a pair of front permanent joints. Each of the side panels also define a second side margin which is permanently attached to the side edge of the absorbent chassis in the back waist region to provide a pair of back permanent joints. The absorbent article also includes a fastener located in one of the side panels. The absorbent article also includes a line of weakness located in the one side panel separating the fastener from one of the front or the back permanent joints. The fastener is released only after the line of weakness is broken and is configured to refastenably engage the one side panel of the absorbent article to the exterior surface of the absorbent chassis in one of the front waist region or the back waist region of the absorbent article.

In another aspect, the present invention concerns a pant-like, disposable absorbent article which defines a front waist region, a back waist region, a crotch region which extends between and connects the waist regions, a longitudinal direction and a lateral direction. The absorbent article includes an absorbent chassis which defines an absorbent core, an exterior surface, an interior surface opposite the exterior surface, a pair of laterally opposed side edges and a pair of longitudinally opposed waist edges. The absorbent article also includes a pair of laterally opposed extensible back panels which are permanently attached to the side edges of the absorbent chassis in the back waist region of the absorbent article to provide a pair of back permanent joints. The absorbent article also includes a pair of laterally opposed extensible front panels which are permanently attached to the side edges of the absorbent chassis in the front waist region of the absorbent article to provide a pair of front permanent joints. The front panel and the back panel on each side edge of the absorbent chassis are also permanently connected together at a side seam to provide a pair of side permanent joints and to define a waist opening and a pair of leg openings to provide the pant-like, disposable absorbent article. The absorbent article also includes a fastener located in each of the front panels. The absorbent article also includes a line of weakness in each of the front panels and separating the fasteners from the front permanent joints. The fasteners are released only after the lines of weakness are broken and are configured to refastenably engage the front panels to the exterior surface of the absorbent chassis in the front waist region of the absorbent article.

In yet another aspect, the present invention concerns a pant-like, disposable absorbent article which defines a front waist region, a back waist region, a crotch region which extends between and connects the waist regions, a longitudinal direction and a lateral direction. The absorbent article includes an absorbent chassis which defines an absorbent core, an exterior surface, an interior surface opposite the exterior surface, a pair of laterally opposed side edges and a pair of longitudinally opposed waist edges. The absorbent article also includes a pair of laterally opposed extensible back panels which are permanently attached to the side edges of the absorbent chassis in the back waist region of the absorbent article to provide a pair of back permanent joints. The absorbent article also includes a pair of laterally opposed extensible front panels which are permanently attached to the side edges of the absorbent chassis in the front waist region of the absorbent article to provide a pair of front permanent joints. The front panel and the back panel on each side edge of the absorbent chassis are also permanently connected together at a side seam to provide a pair of side permanent joints and to define a waist opening and a pair of leg openings to provide the pant-like, disposable absorbent article. The absorbent article also includes a fastener located in each of the back panels adjacent the side permanent joints. The absorbent article also includes a line of weakness located in each of the back panels and separating the fasteners from the side permanent joints. The fasteners are released only after the lines of weakness are broken and are configured to refastenably engage the back panels to the front waist region of the absorbent article.

The present invention advantageously provides pant-like, disposable absorbent articles which include a fastener and a line of weakness. In particular, the present invention provides pant-like disposable absorbent articles which are capable of being reliably pulled up or down over the hips of the wearer to assist in the toilet training of the wearer similar to conventional training pants. Moreover, similar to conventional diapers, some configurations of the pant-like disposable absorbent articles of the present invention can be advantageously applied to and removed from the wearer similar to conventional diapers. Further, the pant-like disposable absorbent articles of the present invention allow easy inspection by the caregiver to assist in determining whether the article is soiled similar to conventional diapers. As such, the present invention can provide a dual use absorbent article which can function as both a pant-like absorbent article and as a conventional diaper.

Still further, the pant-like disposable absorbent articles of the present invention provide a line of weakness, which eases the opening and removal of the pant-like disposable absorbent article. Therefore, the pant-like diaper is presented in and maintains a pant-like configuration, but in particular configurations, the caregiver or the wearer when desired, can readily open the absorbent article for use as a conventional diaper or for removal. Moreover, the lines of weakness assist in identifying to the wearer or the caregiver where the opening for the pant-like absorbent article should be made for the absorbent article to be used in the conventional configuration. Further, upon opening of the line of weakness, the opening edges will maintain a neat appearance rather than a ragged tear, thereby providing a more pleasing diaper appearance when the absorbent article is being used in the conventional configuration. Finally, the fastener may be configured to be provided by other components of the pant-like absorbent article, or combinations thereof. Components which may be used individually or in combination to provide the fastener include the line of weakness, the extensible side panels, and the like. Accordingly, the fastener of the present invention may remain unobtrusive to the wearer while the pant-like absorbent article remains in the pant-like configuration, but upon disengagement of the releasable joint, becomes available to the wearer for use. Further, incorporating the fastener into existing portions of the absorbent article eases manufacturing and reduces excess materials thereby reducing costs.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

FIG. 5-B representatively shows a perspective view of an alternate configuration of the line of weakness and the fastener adjacent the front permanent joint;

FIG. 5-C representatively shows a perspective view of yet another alternate configuration of the line of weakness and the fastener located in the front side panel; and FIG. 5-D representatively shows a perspective view of yet another alternate configuration of the line of weakness and the fastener adjacent the side permanent joint.

DETAILED DESCRIPTION OF THE INVENTION

The present invention concerns pant-like, disposable absorbent articles which are adapted to be worn adjacent to the body of a wearer to absorb and contain various exudates discharged from the body. The pant-like absorbent articles are configured to closely conform to the body of the wearer to effectively contain body exudates while being capable of being pulled up or down over the hips and buttocks of the wearer. The absorbent articles also include at least one line of weakness and at least one fastener such that they can be secured to and removed directly from the waist of the wearer and easily inspected to determine if they have been soiled during use. As such, the pant-like, disposable absorbent articles of the present invention can function in a similar manner to conventional training pants when left in the pant-like configuration. Alternatively, in certain configurations, the lines of weakness may be opened, and the fasteners used to allow the disposable absorbent articles of the present invention to be applied similar to a conventional diaper. As used herein, the term "disposable" refers to articles which are intended to be discarded after a limited use and which are not intended to be laundered or otherwise restored for reuse.

The pant-like disposable absorbent articles of the present invention will be described in terms of a disposable, pant-like diaper article which is adapted to be worn by infants about the lower torso. In particular, the pant-like disposable absorbent articles will be described in terms of a pant-like, disposable diaper having side panels, at least one line of weakness and at least one fastener. It is understood that the articles and methods of the present invention are equally adaptable for other types of absorbent articles such as adult incontinent products, training pants, feminine hygiene products, other personal care or health care garments, and the like.

Figure 1:
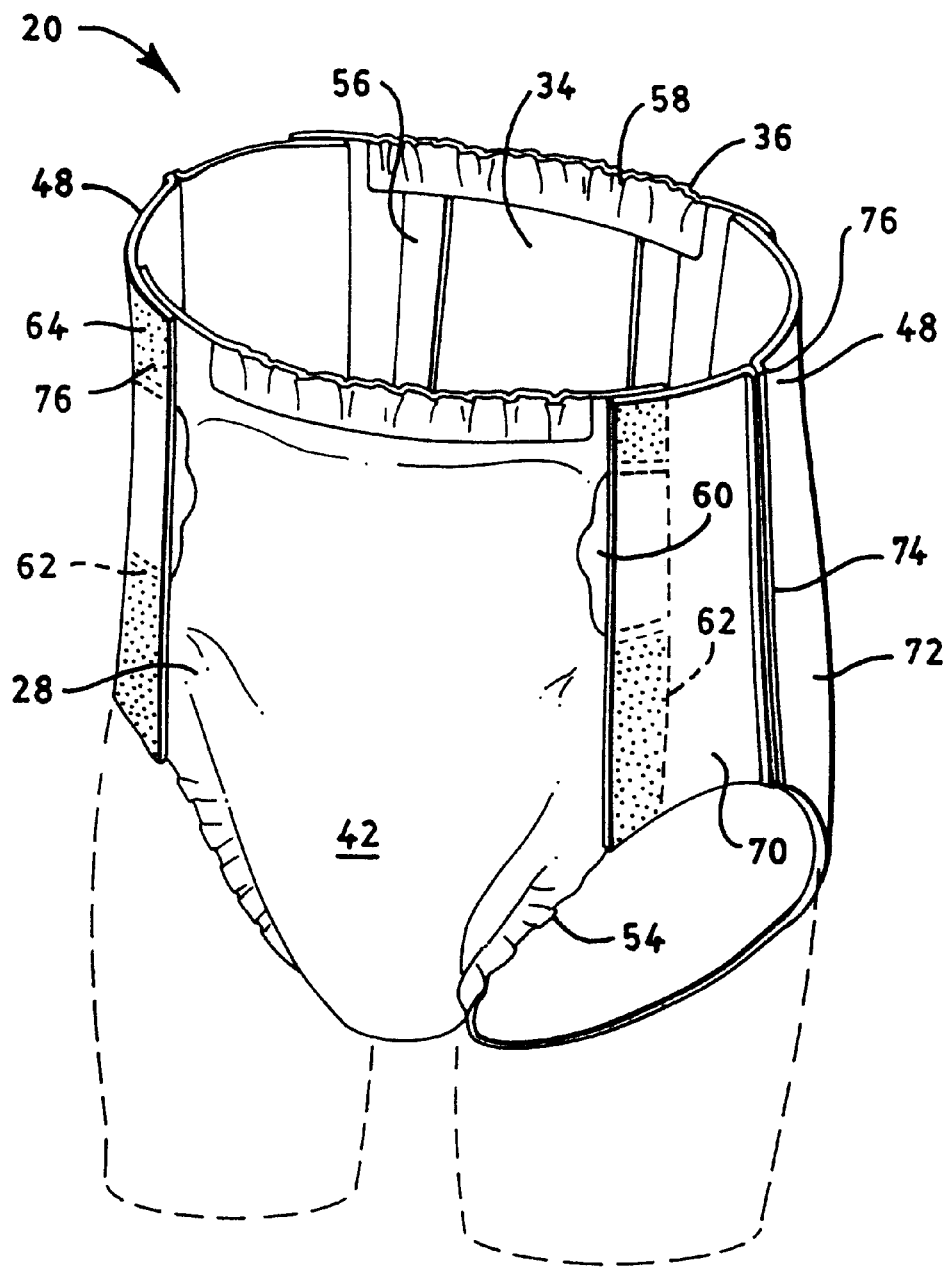
FIG. 1 representatively shows a perspective view of an example of a pant-like, disposable absorbent article of the present invention.
Figure 2:
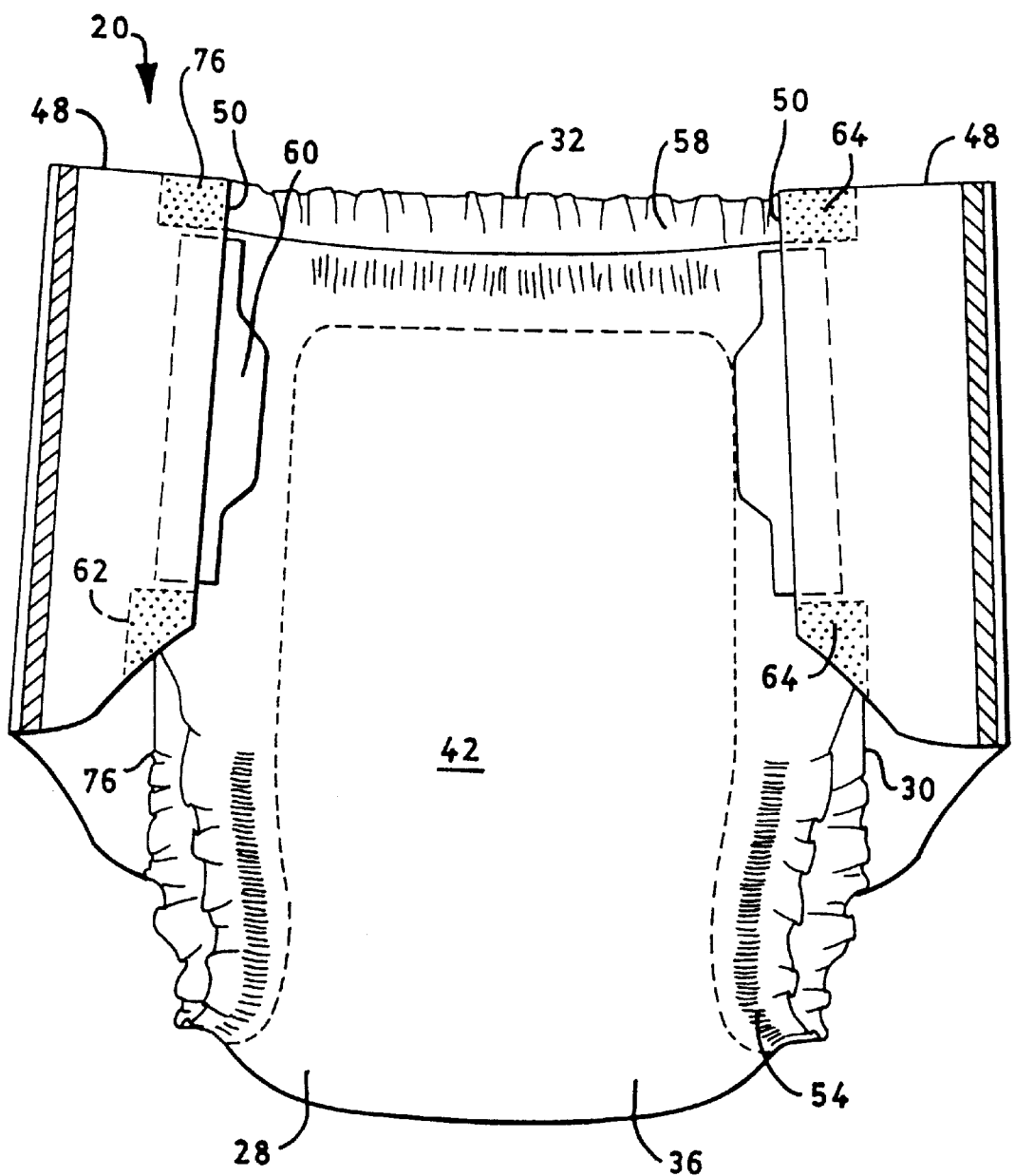
FIG. 2 representatively shows a front plan view of the pant-like, disposable absorbent article of FIG. 1.
Figure 3:
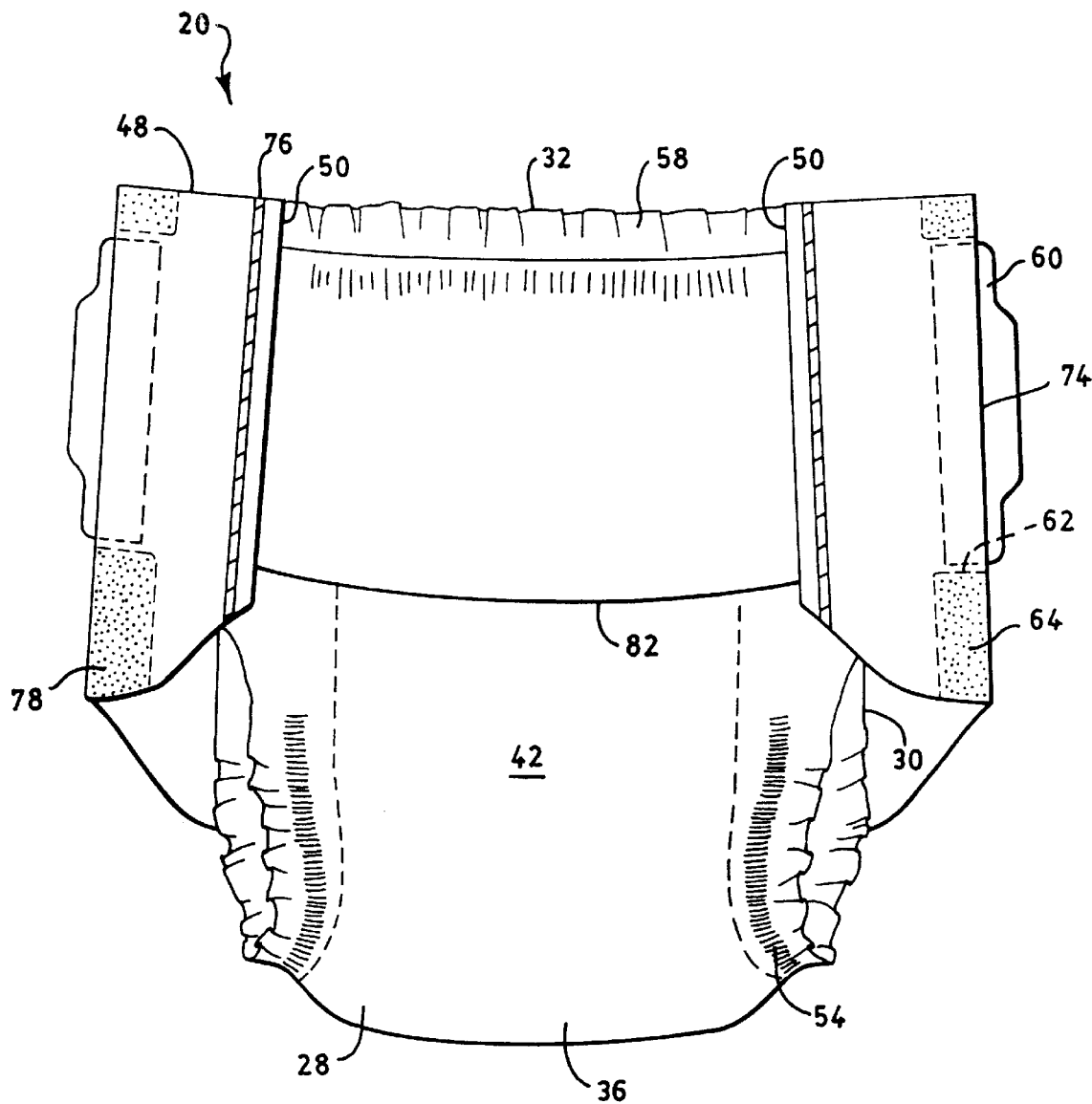
FIG. 3 representatively shows a front plan view of an alternate configuration of the absorbent article, wherein the line of weakness and the fasteners are located at the side seams.
Figure 4:
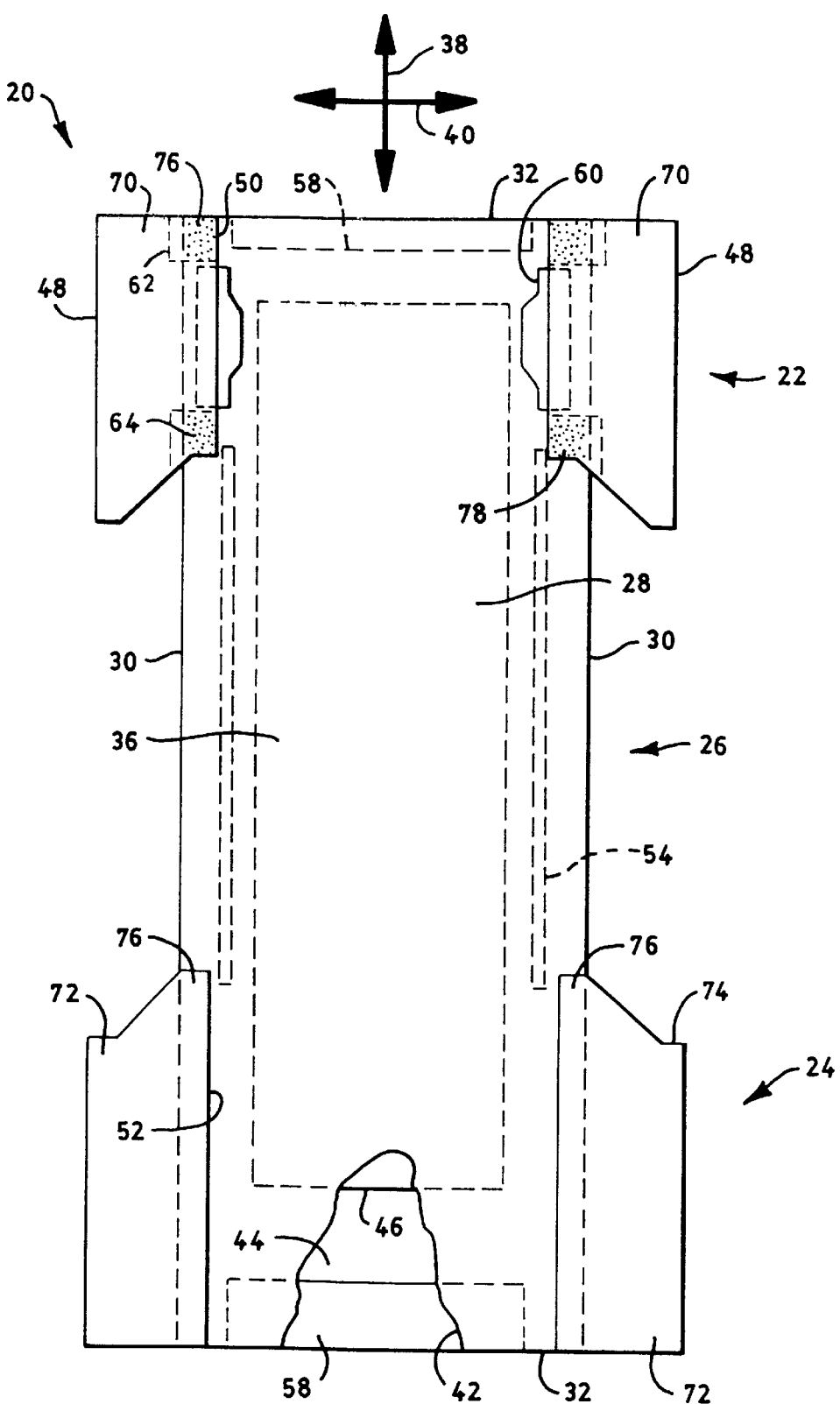
FIG. 4 representatively shows a plan view of the disposable absorbent article of FIG. 1 with the side permanent joints broken and in a stretched and laid flat condition with the surface of the article which contacts the wearer's clothing facing the viewer and with portions of the article partially cut away to show the underlying features.

FIG. 1 representatively illustrates an example of a pant-like, disposable diaper, as generally indicated at 20, of the present invention. FIG. 2 representatively illustrates a front plan view of the pant-like diaper of FIG. 1. FIG. 3 representatively illustrates a front plan view of an alternative configuration of the pant-like diaper 20. FIG. 4 representatively illustrates the pant-like diaper of FIG. 1 in an opened, stretched and laid flat configuration with the surface of the diaper adapted to contact the wearer's clothing facing the viewer and with portions of the diaper partially cut away to show the underlying features. As illustrated in FIG. 4, the diaper 20 defines a front waist region 22, a back waist region 24, a crotch region 26 which extends between and connects the front and back waist regions 22 and 24, a longitudinal direction 38 and a lateral direction 40. The illustrated pant-like diaper 20 includes an absorbent chassis 28 and a pair of laterally opposed side panels 48. The absorbent chassis 28 defines a pair of laterally opposed side edges 30, a pair of longitudinally opposed waist edges 32, an interior surface 34 which is configured to contact the wearer, and an exterior surface 36 opposite the interior surface 34 which is configured to contact the wearer's clothing in use. The absorbent chassis 28, as representatively illustrated in FIG. 4, includes an outer cover 42, a bodyside liner 44 which is connected to the outer cover 42 in a superposed relation, and an absorbent core 46 which is located between the outer cover 42 and the bodyside liner 44. The side panels 48 extend laterally outward from and between each opposed side edge 30 of the absorbent chassis 28 in the front and back waist regions 22 and 24.

The front waist region 22 comprises the portion of the diaper 20 which, when worn, is positioned on the front of the wearer while the back waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer. The side panels 48 comprise the portions of the diaper which, when worn, are positioned on the side hip regions of the wearer. The laterally opposed side edges 30 of the absorbent chassis 28 and the side panels 48 of the diaper 20 generally define leg openings which may be curvilinear. The waist edges 32 of the absorbent chassis 28 of the diaper 20 and the side panels 48 are configured to encircle the waist of the wearer when worn and provide a waist opening when attached or fastened which defines a waist perimeter dimension.

As illustrated in FIGS. 1,2, and 4, at least one of the side panels 48 of the pant-like diaper 20 includes at least one line of weakness 62 in combination with a fastener 60. The side panels 48 are permanently attached to the side edge 30 of the absorbent chassis 28 in one of the waist regions 22 or 24 via permanent bonds 64 to provide a permanent joint 76. The at least one line of weakness 62 further provide a method for opening the pant-like diaper for use in a conventional configuration. The pant-like diaper 20 further includes at least one fastener 60 located adjacent the at least one line of weakness 62. The fastener 60 is configured to be available for use after the line of weakness is opened. The illustrated diaper 20 of the present invention may further include an attachment panel 82 located on the exterior surface 36 of the absorbent chassis 28 to which the fastener 60 is configured to releasably engage.

The absorbent chassis 28 is configured to contain and/or absorb any body exudates discharged from the wearer. Whereas, the side panels 48, permanent joints 76, and the fasteners 60 are configured to maintain the diaper 20 about the waist of the wearer and provide a pant-like appearance. The diaper 20 may further include leg elastics 54, containment flaps 56 and waist elastics 58 as are known to those skilled in the art. It should be recognized that individual components of the diaper 20 may be optional depending upon the intended use of the diaper 20.

The pant-like diaper 20 may be of various suitable shapes. For example, in the opened configuration as illustrated in FIG. 4, the diaper may have an overall rectangular shape, T-shape or an approximately hour-glass shape. In the shown embodiment, the diaper 20 has a generally I-shape in an unfastened configuration. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic and thermal bonds or combinations thereof. In the shown embodiment, for example, the outer cover 42 and bodyside liner 44 are assembled to each other and to the absorbent core 46 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Alternatively, the absorbent core 46 may be connected to the outer cover 42 using conventional fasteners such as buttons, hook and loop type fasteners, adhesive tape fasteners, and the like. The other components of the diaper 20 may be suitably connected together using similar means. Similarly, other diaper components, such as the elastic members 54 and 58 and the fasteners 60, may be assembled into the diaper 20 article by employing the above-identified attachment mechanisms. Desirably, the majority of the diaper components are assembled together using ultrasonic bonding techniques for reduced manufacturing cost.

The outer cover 42 of the absorbent chassis 28 of the pant-like diaper 20, as representatively illustrated in FIGS. 1–4, may suitably be composed of a material which is either liquid permeable or liquid impermeable. It is generally preferred that the outer cover 42 be formed from a material which is substantially impermeable to liquids. A typical outer cover can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). If it is desired to present the outer cover 42 with a more clothlike feeling, the outer cover 42 may comprise a polyolefin film having a nonwoven web laminated to the exterior surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers. The polypropylene fibers have a thickness of about 1.5 to 2.5 denier per filament, which nonwoven web has a basis weight of about 17 grams per square meter (0.5 ounce per square yard). The outer cover 42 may otherwise include bicomponent fibers such as polyethylene/polypropylene bicomponent fibers. Methods of forming such clothlike outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent core 46. Still further, the outer cover 42 may optionally be composed of a micro-porous "breathable" material which permits vapors to escape from the absorbent 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868 issued to McCormack et al. and U.S. Pat. No. 5,843,056 issued Dec. 1, 1998 to Good et al., the descriptions of which are hereby incorporated by reference. Still further, the outer cover 42 may also be an elastomeric material such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference. The outer cover 42 can also be embossed or otherwise provided with a matte finish to provide a more aesthetically pleasing appearance.

The bodyside liner 44, as representatively illustrated in FIG. 4, suitably presents a bodyfacing surface which is compliant, soft feeling, and nonirritating to the wearer's skin. Further, the bodyside liner 44 may be less hydrophilic than the absorbent core 46, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example , polyester or polypropylene fibers), or a combination of natural and synthetic fibers. The bodyside liner 44 is suitably employed to help isolate the wearer's skin from liquids held in the absorbent core 46.

Various woven and nonwoven fabrics can be used for the bodyside liner 44. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 44 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or the like. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto to which is configured to treat or be transferred to the wearer's skin.

The absorbent core 46 of the pant-like diaper 20, as representatively illustrated in FIG. 4, may suitably comprise a matrix of hydrophilic fibers, such as a web of cellulosic fluff, mixed with particles of a high-absorbency material commonly known as superabsorbent material. In a particular embodiment, the absorbent core 46 comprises a matrix of cellulosic fluff, such as wood pulp fluff, and superabsorbent hydrogel-forming particles.

The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent core 46 to better contain and absorb body exudates. The concentration of the superabsorbent particles may also vary through the thickness of the absorbent core 46. Alternatively, the absorbent core 46 may comprise a laminate of fibrous webs and superabsorbent material or other suitable means of maintaining a superabsorbent material in a localized area.

The absorbent core 46 may have any of a number of shapes. For example, the absorbent core may be rectangular, I-shaped, or T-shaped. It is generally preferred that the absorbent core 46 be narrow in the crotch area of the diaper 20. It has been found that the absorbent core 46 of the present invention is particularly useful when the width dimension in the crotch region 26 is from about 2.5 to about 12.7 centimeters (1.0 to about 5.0 inches), and desirably no more than about 7.6 centimeters (3.0 inches). The narrow crotch width dimension of the absorbent core 46 allows the absorbent chassis 28 to better fit between the legs of the wearer. The size and the absorbent capacity of the absorbent core 46 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding; and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Virginia and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent core 46.

Optionally, a substantially hydrophilic tissue wrapsheet (not illustrated) may be employed to help maintain the integrity of the airlaid fibrous structure of the absorbent core 46. The tissue wrapsheet is typically placed about the absorbent core over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent core. The wrapsheet material on one side of the absorbent fibrous mass may be bonded to the wrapsheet located on the opposite side of the fibrous mass to effectively entrap the absorbent core 46.

As representatively illustrated in FIG. 1, the absorbent chassis 28 of the pant-like diaper 20 may include a pair of containment flaps 56 which are configured to provide a barrier to the lateral flow of body exudates. The containment flaps 56 may be located along the laterally opposed side edges 30 of the absorbent chassis 28. Each containment flap 56 typically defines an unattached edge which is configured to maintain an upright, perpendicular configuration in at least the crotch region 26 of the diaper 20 to form a seal against the wearer's body. The containment flaps 56 may extend longitudinally along the entire length of the absorbent chassis 28 or may only extend partially along the length of the absorbent chassis 28. When the containment flaps 56 are shorter in length than the absorbent chassis 28, the containment flaps 56 can be selectively positioned anywhere along the side edges 30 of the absorbent chassis 28. In a particular aspect of the invention, the containment flaps 56 extend along the entire length of the absorbent chassis 28 to better contain the body exudates.

Such containment flaps 56 are generally well known to those skilled in the art. For example, suitable constructions and arrangements for containment flaps 56 are described in U.S. Pat. No. 4,704,116 issued Nov. 3, 1987, to K. Enloe the disclosure of which is hereby incorporated by reference.

The disposable pant-like diaper 20 of the different aspects of the present invention may further include elastics at the waist edges 32 and side edges 30 of the absorbent chassis 28 to further prevent leakage of body exudates and support the absorbent chassis 28. For example, as representatively illustrated in FIGS. 1–4, the pant-like diaper 20 of the present invention may include a pair of leg elastic members 54 which are connected to the laterally opposed side edges 30 of the absorbent chassis 28 in the crotch region 26 of the diaper 20 and a pair of waist elastic members 58 which are connected to the longitudinally opposed waist edges 32 of the absorbent chassis 28 of the diaper 20. The leg elastics 54 and waist elastics 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastics 58 are well known to those skilled in the art. Exemplary of such materials are sheets or strands or ribbons of a polymeric, elastomeric material which are adhered to the outer cover 42 in a stretched position, or which are attached to the outer cover 42 while the outer cover is pleated, such that elastic constrictive forces are imparted to the outer cover 42. The leg elastics may also include such materials as polyurethane, synthetic and natural rubber.

As representatively illustrated in FIGS. 1–4, the pant-like diaper 20 further includes a pair of laterally opposed side panels 48. Each side panel 48 defines a first side margin 50 which is permanently attached to the side edge 30 of the absorbent chassis 28 in the front waist region 22 and a second side margin 52 which is permanently attached to the side edge 30 of the absorbent chassis 28 in the back waist region 24 to provide a pair of permanent joints 76.

Alternatively, each of the side panels 48 may include one or more individual, distinct pieces of material. For example, in the illustrated embodiments, each side panel 48 includes a front side panel 70 and a back side panel 72. The illustrated front side panel 70 includes the first side margin 50 which is permanently attached to the side edges 30 of the absorbent chassis 28 in the front waist region 22 of the diaper 20 to provide the front permanent joint 76. The illustrated back side panel 72 includes the second side margin 52 which is permanently connected to the side edges 30 of the absorbent chassis 28 in the back waist region 24 of the diaper 20 to provide the back permanent joint 76. In such a configuration, the laterally outward edge of each front side panel 70 is connected to the laterally outward edge of each back side panel 72 to provide a side seam 74 as illustrated in FIGS. 1–3, and 5C–5D. Side panels 48 having such front and back side panels 70 and 72 provide improved manufacturability. In an alternative configuration, each side panel 48 may include a single piece of material which is folded over upon itself during manufacturing along a fold line located in a similar location to the side seam 74.

The side seams 74 of the present invention may be arranged in a number of configurations. For example, as representatively illustrated in FIGS. 1–3 and 5C–5D, the side seams 74 may be provided in a flange bonded configuration. In the illustrated embodiments the interior surface of the front panel 70 is attached to the interior surface of the back panel 72 in an overlapping configuration to provide the flanged side seams 70. Alternatively, the side seams 74 may be provided in a lap bonded configuration. As such, the exterior surface 36 of one of the front or back panels 70 and 72 are bonded to the interior surface 34 of the opposing front or back panel 70 and 72 in an overlapping arrangement. For example, the side seams 74 may be provided in a lap bonded configuration (not illustrated). Such a configuration may be desirable as a lap bonded configuration would subject the side seams 74 primarily to shear forces during use, thereby providing enhanced seam strength.

Materials suitable for the side panels 48 of the diaper 20 are generally known to those skilled in the art. For example, suitable materials for the side panels 48 include those materials described above as being suitable for the outer cover 42 or bodyside liner 44 of the absorbent chassis 28 of the diaper 20 such as woven and nonwoven materials or laminates of such materials. Desirably, the side panels 48 are elastic or stretchable to provide improved fit about the wearer. For example, the side panels 48 may comprise a stretch-thermal laminate (STL), neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference. When made with elastic materials, the side panels 48 are desirably capable of elongating in the lateral direction 40 from about 10 to about 400 percent, more desirably at least about 100 percent, even more desirably from about 100 to about 300 percent, and still yet more desirably from about 150 to about 250 percent for improved fit and performance. The stretchability of the side panels allows the side panels 48 to stretch over and around the hips of the wearer as the pant-like diaper is pulled on while still maintaining proper fit at the waist after the diaper is correctly positioned on the wearer.

Alternatively, the side panels 48 may be provided by a portion of the absorbent chassis 28 such as the outer cover 42, bodyside line 44 or a combination thereof (not illustrated). For example, the side panels 48 may be provided by the outer cover 42. As such, the outer cover 42 in the front or back waist region 22 and 24 may extend beyond the side edges 30 of the absorbent chassis 28 in the lateral direction 40 and be permanently attached to the front or back waist region 22 and 24 of the diaper 20 to provide a pair of permanent joints 76.

Desirably, the side panels 48 are a neck-bonded laminate material for improved manufacturing due to it's ability to stretch in the cross machine direction. For example, in a particular embodiment, the side panels 48 include a neck-bonded laminate material which includes a urethane film having a basis weight of about 15 grams per square meter and commercially available from Shawmut Mills, a business having offices in West Bridgewater Massachusetts, under the trade designation SHAWMUT TX-1560 sandwiched between two layers of necked, stretched spunbond. Each spunbond layer has a basis weight of about 16 grams per square meter and is composed of 3.0 denier polypropylene fibers. The composite is laminated together with an adhesive spray at an add-on rate of about 0.3 grams per square meter. A suitable adhesive is available from Findley Adhesive under the trade designation FINDLEY 2525A. Such a neck-bonded laminate material is generally capable of elongating in the cross machine direction about 185 percent.

Figure 5A:
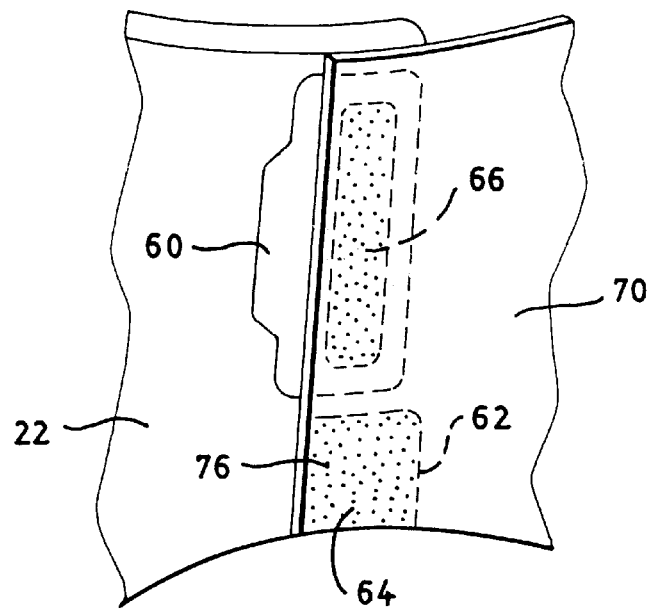
FIG. 5-A representatively shows a perspective view of the line of weakness and the fastener adjacent the front permanent joint.
Figure 5B:
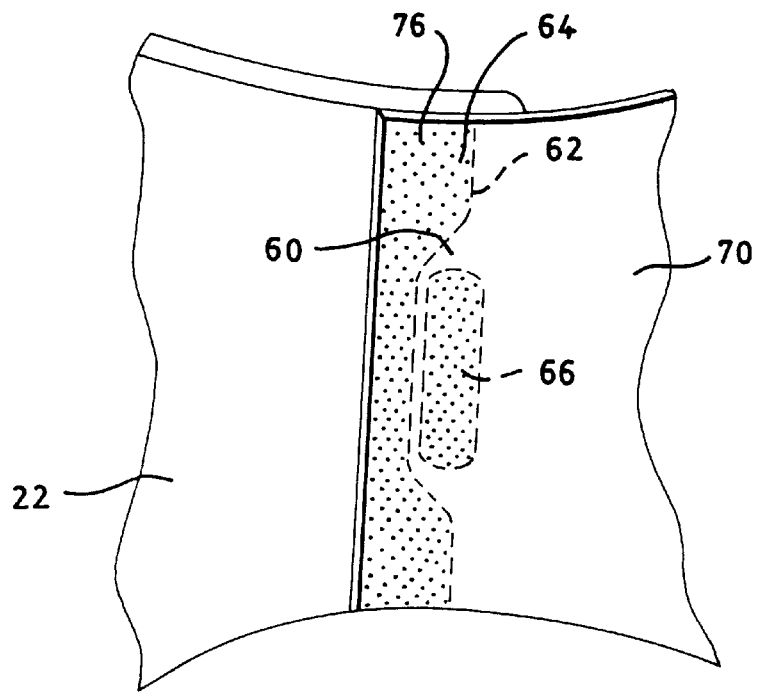
Figure 5C:
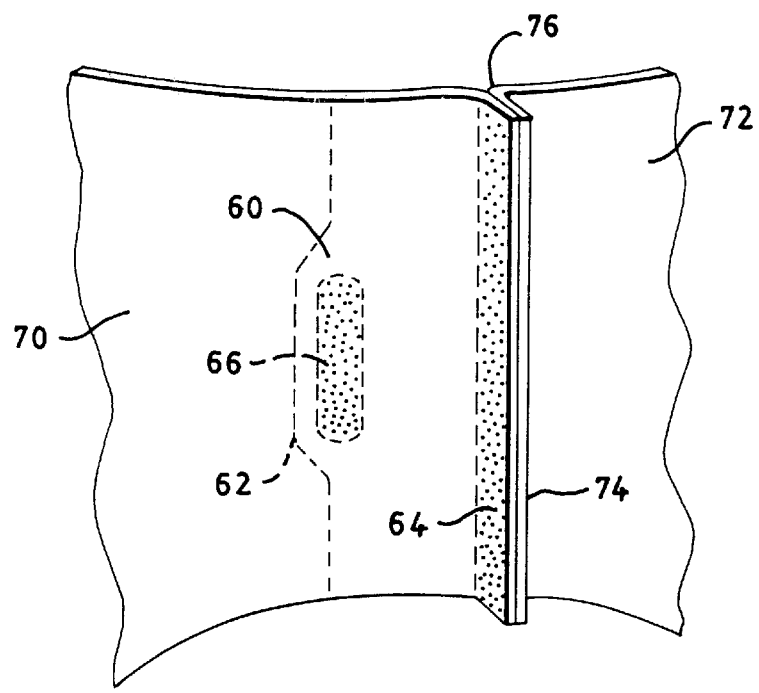

The permanent joints 76 of the present invention, including the front, back and side permanent joints 76 may be comprised of permanent bonds 64. For example, as representatively illustrated in FIGS. 5B–5D, the permanent joints 76 may be provided by a continuous permanent bond 64 which runs in the longitudinal direction 38 from the waist opening to the leg opening. Alternatively, the permanent bonds 64 may be provided intermittently within the permanent joint 76. For example, the permanent bonds 64 may be pockets of discrete point bonds, dashed lines, continuous lines, discontinuous lines and the like, or combinations thereof. Moreover, the bonds may have any shape such as circular, square, triangular and the like, or combinations thereof. The permanent bonds 64 may be provided by any type of bonding, such as adhesive, thermal and ultrasonic bonding as are well known to those skilled in the art. Desirably, the bonds are ultrasonic bonds for improved manufacturing efficiency.

Alternatively, as representatively illustrated in FIGS. 1–5A the permanent joints 76 may be provided by a combination of permanent bonds 64 and the fastener 60 as will be discussed in more detail below. As such, the fastener 60 may assist the permanent bonds 64 in providing the permanent joints 76 by being provided adjacent to or aligned with the permanent bonds 64. As such, the permanent joint 76 may be provided by any combination of permanent bonds 64 and fasteners 60 as are well known to those skilled in the art.

The pant-like disposable diaper 20 of the different aspects of the present invention further includes at least one fastener 60 in one of the side panels 48 for securing the absorbent article about the waist of the wearer. Desirably, the diaper 20 includes a pair of fasteners 60 located in each of the side panels 48 as illustrated in FIGS. 1–4 for improved fit and performance. The fasteners 60 of the present invention are configured to be available for use upon the disengagement of the line of weakness 62, as will be discussed in more detail below. The fasteners 60 provide the diaper 20 with the ability to provide the ease of application of a pant-like absorbent article while yet being capable of providing the fit and comfort of a conventional diaper type absorbent article when the care-giver or the wearer chooses to use it as such.

The fasteners 60 may be comprised of a single piece of material or a plurality of pieces. In addition, a portion of the diaper 20 may assist in providing the fastener 60. For example, as representatively illustrated in FIGS. 5B–D the fastener 60 may be provided by the combination of a fastening member 66 attached to a portion of the side panels 48. Moreover, the fastener 60 may be fashioned in various shapes and sizes as are known to those skilled in the art. For example, as representatively illustrated in FIGS. 1–5A, the fastener 60 may be generally rectangular in shape. Alternatively, as representatively illustrated in FIGS. 5B–D, the fastener 60 may define other contours such as curvilinear, or the like.

Desirably, the fastener 60 of the present invention may feature the ability to be extensible in at least the lateral direction 40. For example, as discussed above, the fastener 60 may be provided by a combination of a fastening member 66 and a portion of the side panels 48, which may be extensible. Accordingly, the extensible side panels 48 may, in turn, provide extensibility for the fastener 60. Alternatively, the fastener 60 may itself be configured to be extensible in at least the lateral direction. As such the fastener 60 may define a different degree of extensibility than the side panels 48. In yet another alternative, the fasteners 60 may include an extensible panel (not illustrated) which may provide the fasteners 60 with a different degree of extensibility than the side panels 48. When the fastener 60 features extensibility in at least the lateral direction 40, improved fit and comfort is provided to the wearer by allowing the fastener 60 more flexibility and range in engaging the exterior surface 36 of the absorbent chassis 28 of the diaper 20. If the fastener 60 is provided with an extensible panel, it may be comprised of material well known in the art. The materials may include a stretch-bonded-laminate (SBL) material, a neck-bonded-laminate (NBL) material, an elastomeric film, an elastomeric foam material, or the like such as described above as being suitable for the side panels 48.

Desirably, the fasteners 60 may be configured to refastenably engage directly with the exterior surface of the outer cover 42 of the diaper 20 to provide improved fit and ease of fastening. The fasteners 60 may also be configured to refastenably engage directly with the exterior surface of the side panels 48 of the diaper 20. As such, the wearer or the caregiver may be provided with yet an even greater surface area for the fasteners 60 to engage, thereby further improving the fit and ease of fastening of the diaper 20.

In yet another alternative, an attachment panel 82 may be located on the outer cover 42 to which the fasteners are configured to refastenably engage. As representatively illustrated in FIG. 3, the disposable diaper 20 of the present invention may include an attachment panel 82 located on the outer cover 42 in one of the waist regions 22 and 24 on the exterior surface 36 of the diaper 20. In such a configuration, the fasteners 60, are configured to refastenably engage the attachment panel 82 to maintain the diaper 20 about the waist of the wearer after the lines of weakness 62 are broken and the fasteners 60 are available for use. The attachment panel 82 may include two separate panels located along the opposed side edges 30 of the diaper 20 in one of the waist regions 22 and 24 of the diaper 20. Alternatively, the attachment panel 82 may include a single piece of material that extends substantially across the respective waist region of the diaper 20.

Suitable fastening materials, which contribute to providing the fastener 60, are well known to those skilled in the art and can include adhesive tape tab fasteners, hook and loop fasteners, mushroom fasteners, snaps, pins, belts and the like, and combinations thereof. For example, in the illustrated embodiments, the fastener 60 and/or the fastening member 66 may be hook type fasteners and the outer cover 42 or attachment panel 82 may be configured to function as a complimentary loop type fastener. Desirably, the fasteners 60 are hook type fasteners which are refastenably engageable directly with the outer cover 42. Such an arrangement provides the ability to vary the size of the waist opening in very small increments over a wide range to fit the waist of the wearer.

The pant-like disposable diaper 20 of the different aspects of the present invention further includes at least one line of weakness 62 in one of the side panels 48. Desirably, the diaper 20 includes a line of weakness 62 and a fastener 60 in each side panel 48. For example, as representatively illustrated in FIGS. 1–4, each of the front side panels 70 includes a line of weakness 62. Alternatively, as representatively illustrated in FIGS. 5C–5D, the line of weakness 62 may be located in one or both of the back side panels 72.

The lines of weakness 62 may be comprised of one or more lines of weakness 62. For example, as representatively illustrated in FIGS. 1–4, the diaper 20 includes a pair of distinct lines of weakness 62 located on each of the side panels 48. Alternatively, as Representatively illustrated in FIGS. 5A–5D, the lines of weakness 62 may be comprised of a single continuous line of weakness.

The diaper 20 is provided in a pant-like configuration with the lines of weakness 62 intact. In such a configuration, the diaper 20 may be pulled on or off over the legs and hips of the wearer. Further the lines of weakness 62 should have relatively low strength such that the joint, may be broken by the caregiver if desired without tearing or severely damaging the other portions of the diaper 20. However, the strength of the lines of weakness 62 should be great enough such that they do not release until intentionally broken by the caregiver. As such, the lines of weakness 62 may be broken to inspect the diaper for possible soiling. If the diaper 20 is soiled during use, the lines of weakness 62 may be broken to easily remove the diaper 20 from the waist of the wearer with reduced risk of undesirably soiling the clothes or legs of the wearer. Finally, the lines of weakness 62 may also be disengaged to allow the user the option of applying the pant-like diaper 20 in a conventional diaper configuration.

The lines of weakness 62 may be located anywhere on the side panels 48 as is well known in the art. For example, as representatively illustrated in FIG. 5C the lines of weakness may be located generally in the middle of the front or rear side panel 70 and 72. Alternatively, the lines of weakness may be located adjacent one of the permanent joints 76. For example, as representatively illustrated in FIGS. 1–5B, and 5D, the lines of weakness may be located adjacent the front or side permanent joints 76. In yet another alternative, the lines of weakness 62 may be located within the first or second side margin 50 and 52 of the side panels 48. Desirably, as representatively illustrated in FIGS. 1–5B and 5D, the lines of weakness are located between the fasteners 60 and the permanent bonds 64, which provide the permanent joints 76.

Suitable lines of weakness 62 are well known to those skilled in the art and can include perforations, a thinned or scored line of material which may be continuous or discontinuous, an alternative piece of weaker material and the like, or combinations thereof. Desirably, the lines of weakness 62 are provided by perforations for improved performance and ease of use. For example, as representatively illustrated in FIGS. 1–5D, the diaper 20 includes at least one line of perforations to provide the lines of weakness 62. The perforations may consist of ultrasonic apertures, or they may be provided by mechanical perforation means as are well known to those skilled in the art. Moreover, use of lines of weakness 62 may improve manufacturability of the diaper 20 by allowing the permanent bonds 64 to be applied decisively during the manufacturing process. The lines of weakness are provided in combination with the fasteners 60. As such, upon the opening of the lines of weakness 62, the fasteners 60 in the illustrated embodiments are configured to be made available to refastenably engage the side panels 48 of the diaper 20 to the front waist region 22 of the diaper 20. When the side panels 48 and/or the fasteners 60 are extensible, this arrangement advantageously provides the caregiver or the wearer with the stretch from the side panels 48 while refastenably attaching the fasteners 60 to the front waist region 22 of the diaper 20. Therefore, the wearer is provided with a closer and more conforming fit, thereby reducing the possibility of leakage.

Alternatively, the lines of weakness 62 and the fastener 60 may be configured such that fasteners engage the back waist region 24 of the diaper 20. In such a configuration, the fasteners 60 would engage the side panels 48 to the back waist region 24 to provide the diaper 20. This configuration may be advantageous when it is desired that the lines of weakness 62 and the fasteners 60 be located towards the back of the wearer. Such a configuration may be desirable to prevent a wearer from opening the lines of weakness 62 or the fasteners 60 prematurely.

The combination of the fasteners 60 and the lines of weakness 62 may be located anywhere on the side panels 48 of the diaper 20 as is known to those skilled in the art. For example, as representatively illustrated in the illustrated embodiments, the fasteners 60 are permanently attached to the diaper 20 in the side panels 48 adjacent the lines of weakness 62. The lines of weakness 62 thereby separate the fasteners 60 from one of the permanent joints 76. As such, when the lines of weakness 62 are broken, thus opening and providing the diaper 20 in the conventional configuration, the fasteners 60 are made available for use and are configured to refastenably engage the side panels 48 to the exterior surface 36 of either the front waist region 22 or the back waist region 24.

In particular, as representatively illustrated in FIGS. 1–2, and 4–5B, the fasteners 60 and the lines of weakness 62 may be located in the front side panel 70. As such, when the lines of weakness 62 are broken, the fasteners 60 are configured to refastenably engage the front side panel 70 to the exterior surface 36 of the front waist region 22. Desirably, the fasteners 60 and the lines of weakness 62 are located adjacent the front permanent joints 76.

Figure 5D:
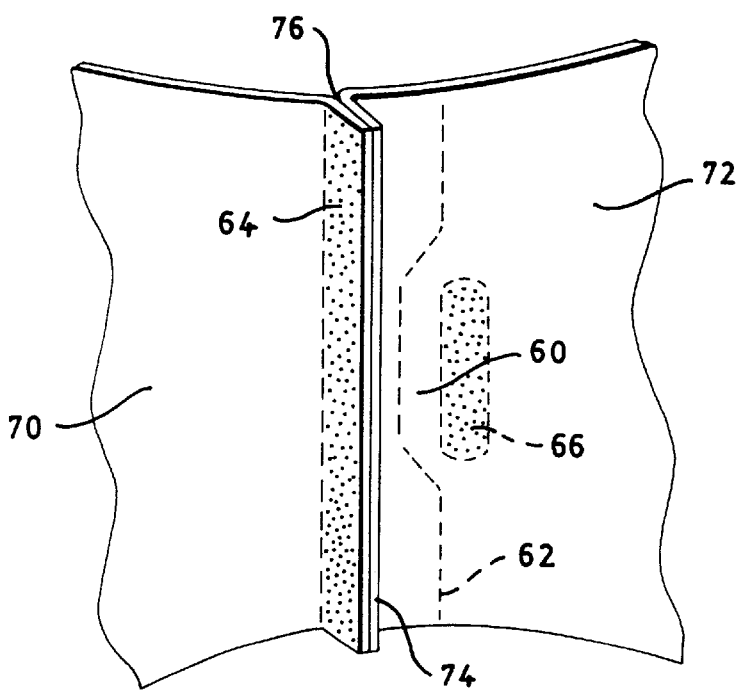

Alternatively, as representatively illustrated in FIG. 5D, the fasteners 60 and the lines of weakness 62 may be located in the back side panel 72. As such, when the lines of weakness 62 are broken, the fasteners 60 are configured to refastenably engage the back side panel 70 to the exterior surface 36 of the front waist region 22. In another alternative, the fasteners 60 may be configured to refastenably engage the back side panel 70 to the exterior surface 36 of the back waist region 24. Desirably, the fasteners 60 and the lines of weakness 62 are located adjacent the side permanent joints 76 with the fasteners 60 configured to engage the front waist region 22.

In yet another alternative, as representatively illustrated in FIG. 3, the fasteners 60 and the lines of weakness 62 may be located within or adjacent the side seams 74, wherein the lines of weakness 62 separate the fastener 60 from the permanent bonds 64 providing the side permanent joints 76. As such, the fasteners 60 may be configured to refastenably engage either the front waist region 22 or the back waist region 24 when the lines of perforations 62 are broken.

The combination of the lines of weakness 62 and the fasteners 60 may be provided in any configuration as is known to those skilled in the art. For example, as representatively illustrated in FIGS. 5B–D the lines of weakness 62 may define a continuous line which extends from the waist opening to the leg opening. Accordingly, the lines of weakness 62 also separate the fasteners 60 from the permanent joints 76 while extending from the waist opening to the leg opening. In such a configuration the lines of weakness 62 may further define the contour of the fastener 60. In particular, the fastener 60 may be comprised of the combination of a fastener member 66 attached to a portion of the side panels, as described above. Upon the breaking of the lines of weakness 62 the fasteners 60 are provided for use to refastenably engage the side panels 48 to the front or back waist regions 22 and 24. Such a configuration may be desirable by providing a neat diaper appearance when in the pant like configuration. The fasteners 60 are unobtrusive while the diaper 20 is used in the pant-like arrangement, while being readily available and obvious upon the opening of the lines of weakness 62.

Alternatively, the lines of weakness 62 may only partially surround the permanent bonds 64 comprising the permanent joints 76. As such, the lines of weakness 62 separate the fasteners 60 from the permanent joints 76 by only isolating the permanent bonds 64 from the fasteners 60. For example, as representatively illustrated in FIGS. 1–5A, the lines of weakness 62 are limited to only partially surrounding the permanent bonds 64 providing the permanent joints 76. As such, the pant like diaper 20 is opened for use in the conventional configuration when the lines of weakness 62, which are limited to only at least partially surrounding the permanent bonds, are broken, thereby also making the fasteners 60 available for use.

In such a configuration, the permanent joint 76 may be provided by a single permanent bond 64, partially surrounded by a single line of weakness 62, and a fastener 60. For example, as representatively illustrated in FIG. 5A, the permanent joint 76 may be provided by the fastener 60 and a single permanent bond 64, which is partially surrounded by a line of weakness 62 to separate it from the fastener 60. As such, when the line of weakness 62 is opened, the fastener 60 is made available for use and the diaper 20 is in the conventional configuration. Alternatively, the permanent joint 76 may be provided by a plurality of permanent bonds 64. For example, as representatively illustrated in FIGS. 1–4, the permanent joint 76 is provided by a fastener 60 located between a pair of permanent bonds 64, each partially surrounded by a line of weakness 62 to separate them from the fastener 60. As such, the diaper 20 is open for use in the conventional configuration when all the lines of perforation 62 are opened, thus also releasing the fasteners 60 for use.

In a particular embodiment, representatively illustrated in FIG. 3, the side seams 74 may each include two longitudinally spaced apart permanent bonds 64 providing the side permanent joint 76, with the fastener 60 located between the two permanent bonds 64. In addition, each side seam includes a line of weakness 62 partially surrounding each of the permanent bonds 64. As such, the lines of weakness separate the fasteners 60 from each of the permanent bonds 64. Accordingly, upon the opening of the lines of weakness 62, the diaper 20 is provided in the conventional configuration, and the fasteners 60 are made available for use to releasably attach the side panels 48 to the exterior surface 36 of the front waist region 22.

The different aspects of the present invention advantageously provide pant-like, disposable absorbent articles which can include the combination of lines of weakness and fasteners. The absorbent article is provided in the prefastened, pant-like configuration to allow the absorbent article to be pulled up or down over the hips of the wearer such as conventional training pants. Yet, the lines of weakness may be disengaged to allow the diaper to be used and applied as a conventional diaper. Moreover, upon opening the lines of weakness, the fasteners can be used to refastenably engage and adjust the front and back waist portions of the absorbent article to maintain the absorbent article about the waist of the wearer after the article has been pulled on in a similar manner to conventional diapers.

As a result, the absorbent articles of the present invention are designed to be capable of being reliably pulled up or down over the hips of the wearer to assist in the toilet training of the wearer. Moreover, similar to conventional diapers, the absorbent articles of the present invention can advantageously be applied to and removed from the wearer with relative ease and cleanliness. As such the present invention provides an absorbent article which performs the dual functions of a pant-like absorbent article and a conventional training pants.

While the invention has been described in detail with respect to specific aspects thereof, it will be appreciated that those skilled in the art, upon attaining an understanding of the fore going, may readily conceive of alterations to, variations of and equivalents to these aspects. Accordingly, the scope of the present invention should be assessed as that of the appended claims and any equivalents thereto.

We claim:

1. A pant-like, disposable absorbent article which defines a front waist region, a back waist region, a crotch region which extends between and connects said waist regions, a longitudinal direction and a lateral direction, said absorbent article comprising:
   a) an absorbent chassis which defines an absorbent core, an exterior surface, an interior surface opposite said exterior surface, a pair of laterally opposed side edges and a pair of longitudinally opposed waist edges;
   b) a pair of opposed side panels which extend laterally outward from said side edges of said absorbent chassis and connect said front waist region to said back waist region to define a waist opening and a pair of leg openings in said pant-like disposable absorbent article, wherein each of said opposed side panels defines a first side margin which is permanently attached to said side edge of said absorbent chassis in said front waist region to provide a pair of front permanent joints and a second side margin which is permanently attached to said side edge of said absorbent chassis in said back waist region to provide a pair of back permanent joints;
   c) a fastener located in one of said side panels; and
   d) a line of weakness located in said side panel separating said fastener from one of said front or said back permanent joints, wherein said fastener is released only after said line of weakness is broken, and wherein said fastener is configured to refastenably engage said at least one side panel of said absorbent article to said exterior surface of said absorbent chassis in one of said front waist region or said back waist region of said absorbent article.

2. The absorbent article of claim 1 wherein said fastener is a hook and loop fastener.

3. The absorbent article of claim 2 and further comprising at least one attachment panel which is located on said exterior surface of said absorbent chassis wherein said fastener is configured to refastenably engage said attachment panel.

4. The absorbent article of claim 2 wherein said absorbent chassis includes an outer cover which provides said exterior surface of said absorbent chassis and wherein said fastener is configured to refastenably engage directly to said outer cover of said absorbent chassis.

5. The absorbent article of claim 1 wherein said side panels are extensible at least in said lateral direction.

6. The absorbent article of claim 5 wherein said side panels are a neck bonded laminate material.

7. The absorbent article of claim 1 wherein said fastener is extensible.

8. The absorbent article of claim 7 wherein said side panels are extensible and wherein said fastener defines a different degree of extensibility than said side panels.

9. The absorbent article of claim 1 wherein said fastener is provided by a fastening member attached to a portion of said side panels.

10. The absorbent article of claim 1 wherein said fastener defines a fastener contour, and wherein said fastener contour is at least partially provided by said line of weakness.

11. The absorbent article of claim 10 wherein said fastener contour is curvilinear.

12. The absorbent article of claim 1 wherein said line of weakness defines a continuous line which extends from the waist opening to one of said leg openings.

13. The absorbent article of claim 1 wherein said line of weakness is a line of perforations.

14. The absorbent article of claim 13 wherein said line of perforations are ultrasonic apertures.

15. A pant-like, disposable absorbent article which defines a front waist region, a back waist region, a crotch region which extends between and connects said waist regions, a longitudinal direction and a lateral direction, said absorbent article comprising:
   a) an absorbent chassis which defines an absorbent core, an exterior surface, an interior surface opposite said exterior surface, a pair of laterally opposed side edges and a pair of longitudinally opposed waist edges;
   b) a pair of laterally opposed, extensible back panels which are permanently attached to said side edges of said absorbent chassis in said back waist region of said absorbent article to provide a pair of back permanent joints;
   c) a pair of laterally opposed, extensible front panels which are permanently attached to said side edges of said absorbent chassis in said front waist region of said absorbent article to provide a pair of front permanent joints wherein said front panel and said back panel on each side edge of said absorbent chassis are permanently connected together at a side seam to provide a pair of side permanent joints and to define a waist opening and a pair of leg openings to provide said pant-like, disposable absorbent article;
   d) a fastener located in each of said front panels; and
   e) a line of weakness located in each of said front panels and separating said fasteners from said front permanent joints wherein said fasteners are released only after said lines of weakness are broken and wherein said fasteners are configured to refastenably engage said front panels to said exterior surface of said absorbent chassis in said front waist region of said absorbent article.

16. The absorbent article of claim 15 wherein said fasteners are hook and loop fasteners.

17. The absorbent article of claim 15 wherein said fasteners are extensible.

18. The absorbent article of claim 17 wherein said fasteners define a different degree of extensibility than said front side panels.

19. The absorbent article of claim 15 wherein said fasteners are provided by fastening member attached to a portion of said front side panels.

20. The absorbent article of claim 15 wherein said fasteners each define a fastener contour, and wherein said fastener contour is at least partially provided by said line of weakness.

21. The absorbent article of claim 20 wherein said fastener contour is curvilinear.

22. The absorbent article of claim 15 wherein said lines of weakness are lines of perforations.

23. The absorbent article of claim 22 wherein each of said lines of perforations are ultrasonic apertures.

24. A pant-like, disposable absorbent article which defines a front waist region, a back waist region, a crotch region which extends between and connects said waist regions, a longitudinal direction and a lateral direction, said absorbent article comprising:

a) an absorbent chassis which defines an absorbent core, an exterior surface, an interior surface opposite said exterior surface, a pair of laterally opposed side edges and a pair of longitudinally opposed waist edges;

b) a pair of laterally opposed, extensible back panels which are permanently attached to said side edges of said absorbent chassis in said back waist region of said absorbent article to provide a pair of back permanent joints;

c) a pair of laterally opposed, extensible front panels which are permanently attached to said side edges of said absorbent chassis in said front waist region of said absorbent article to provide a pair of front permanent joints wherein said front panel and said back panel on each side edge of said absorbent chassis are permanently connected together at a side seam to provide a pair of side permanent joints and to define a waist opening and a pair of leg openings to provide said pant-like, disposable absorbent article;

d) a fastener located in each of said back panels adjacent said side permanent joints; and e) a line of weakness located in each of said back panels and separating said fasteners from said side permanent joints wherein said fasteners are released only after said lines of weakness are broken and wherein said fasteners are configured to refastenably engage said back panels to said exterior surface of said absorbent chassis in said front waist region of said absorbent article.

25. The absorbent article of claim 24 wherein said fasteners are hook and loop fasteners.

26. The absorbent article of claim 24 wherein said fasteners are extensible.

27. The absorbent article of claim 26 wherein said fasteners define a different degree of extensibility than said back side panels.

28. The absorbent article of claim 24 wherein said fasteners are provided by a fastening member attached to a portion of said back side panels.

29. The absorbent article of claim 24 wherein said fasteners each define a fastener contour, and wherein said fastener contour is at least partially provided by said line of weakness.

30. The absorbent article of claim 29 wherein said fastener contour is curvilinear.

31. The absorbent article of claim 24 wherein said lines of weakness are a line of perforations.

32. The absorbent article of claim 31 wherein each of said lines of perforations are ultrasonic apertures.

33. The absorbent article of claim 24 wherein each of said side seams include at least two longitudinally spaced apart permanent bonds and wherein said fastener is located in said side seam between said longitudinally spaced apart bonds, and wherein each of said lines of weakness is located between and separates said fasteners from said longitudinally spaced apart permanent bonds.

* * * * *